(12) United States Patent
Avery et al.

(10) Patent No.: US 9,278,054 B2
(45) Date of Patent: Mar. 8, 2016

(54) HAIR CLEANING KIT

(75) Inventors: Andrew Richard Avery, Wirral (GB); Ezat Khoshdel, Wirral (GB); Jordan Todorov Petkov, Wirral (GB); Glyn Roberts, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/238,480

(22) PCT Filed: Jul. 17, 2012

(86) PCT No.: PCT/EP2012/064031
§ 371 (c)(1),
(2), (4) Date: May 28, 2014

(87) PCT Pub. No.: WO2013/026630
PCT Pub. Date: Feb. 28, 2013

(65) Prior Publication Data
US 2014/0283865 A1    Sep. 25, 2014

(30) Foreign Application Priority Data
Aug. 19, 2011   (EP) ..................... 11178055

(51) Int. Cl.
| | |
|---|---|
| *A61K 8/18* | (2006.01) |
| *A61Q 5/00* | (2006.01) |
| *A61Q 7/00* | (2006.01) |
| *A61Q 9/00* | (2006.01) |
| *A45D 19/18* | (2006.01) |
| *A45D 2/00* | (2006.01) |
| *A45D 37/00* | (2006.01) |
| *A61K 8/02* | (2006.01) |
| *A61Q 5/02* | (2006.01) |
| *A61Q 5/12* | (2006.01) |
| *A61K 8/73* | (2006.01) |
| *A61K 8/04* | (2006.01) |
| *A45D 7/00* | (2006.01) |

(52) U.S. Cl.
CPC .............. *A61K 8/02* (2013.01); *A61K 8/0208* (2013.01); *A61K 8/0241* (2013.01); *A61K 8/046* (2013.01); *A61K 8/732* (2013.01); *A61Q 5/02* (2013.01); *A61Q 5/12* (2013.01); *A45D 2007/008* (2013.01); *A61K 2800/546* (2013.01)

(58) Field of Classification Search
CPC ....... A61K 8/02; A61K 8/0208; A61K 8/732; A61K 8/046; A61K 2800/546; A61K 8/0241; A61Q 5/02; A61Q 5/12; A45D 2007/008; A45D 19/00; A45D 2019/0041; A45D 2019/005; A45D 2019/0091; A45D 2200/10; A45D 2200/1036; A45D 2200/1009; A45D 2200/1018; A45D 2200/1027; A45D 2200/25; A45D 33/38; A47L 13/17; A47L 13/16; A45C 11/008

USPC ......... 132/200, 202, 207, 221, 222, 270, 320, 132/333, 286; 15/97.1, 118, 209.1, 229.14; 206/581, 823
See application file for complete search history.

(56) References Cited

U.S. PATENT DOCUMENTS

| | | | |
|---|---|---|---|
| 893,117 A * | 7/1908 | Wanous ................... | 401/266 |
| 3,912,667 A * | 10/1975 | Spitzer et al. ............ | 521/65 |
| 3,954,113 A * | 5/1976 | Bohrer et al. ............ | 132/200 |
| 4,035,267 A * | 7/1977 | Gleckler et al. ......... | 132/202 |
| 4,149,551 A * | 4/1979 | Benjamin et al. ........ | 132/200 |
| 4,206,195 A * | 6/1980 | Bolich et al. ............ | 424/401 |
| 4,445,521 A * | 5/1984 | Grollier et al. .......... | 132/202 |
| 4,450,151 A * | 5/1984 | Shinozawa ................ | 424/46 |
| 4,658,839 A * | 4/1987 | Dallal et al. ............. | 132/203 |
| 5,223,244 A * | 6/1993 | Moro et al. ............... | 424/46 |
| 5,958,384 A | 9/1999 | Holick | |
| 6,062,234 A * | 5/2000 | Finocchiaro et al. ..... | 132/320 |
| 6,063,390 A * | 5/2000 | Farrell et al. ............ | 424/404 |
| 6,440,175 B1 * | 8/2002 | Stanley, III ............. | 8/405 |
| 6,908,491 B2 | 6/2005 | Fischer | |
| 8,043,017 B2 * | 10/2011 | Beierwaltes et al. ..... | 401/17 |
| 8,492,578 B2 | 7/2013 | Glanzmann | |
| 2001/0007655 A1 * | 7/2001 | Paul et al. ............... | 424/70.11 |
| 2001/0047807 A1 * | 12/2001 | Berke et al. ............. | 132/112 |
| 2003/0064091 A1 * | 4/2003 | Kinderdine et al. ..... | 424/443 |
| 2005/0063764 A1 | 3/2005 | McKay | |
| 2005/0196371 A1 | 9/2005 | Decoster et al. | |
| 2005/0208111 A1 * | 9/2005 | Kelly ...................... | 424/443 |
| 2005/0288208 A1 * | 12/2005 | Keenan et al. ........... | 510/439 |

(Continued)

FOREIGN PATENT DOCUMENTS

| | | |
|---|---|---|
| CN | 1196925 A | 10/1998 |
| DE | 20109450 | 1/2002 |

(Continued)

OTHER PUBLICATIONS

PCT International Search Report in PCT application PCT/EP2012/064031,dated Sep. 26, 2013 with Written Opinion.

(Continued)

*Primary Examiner* — Vanitha Elgart
(74) *Attorney, Agent, or Firm* — Karen E. Klumas

(57) ABSTRACT

A kit for cleansing hair comprising: • a) a dry shampoo, in which the dry shampoo comprises a particulate material, preferably aluminum octenyl succinate starch or rice starch, preferably in the form of an aerosol; and • b) a substrate, preferably a flexible sheet comprising a non-woven material, preferably comprising cellulose fiber or polyester fiber and mixtures thereof, the substrate comprising a surfactant selected from the group consisting of nonionic, anionic, amphoteric and mixtures thereof.

11 Claims, 2 Drawing Sheets

(56) References Cited

U.S. PATENT DOCUMENTS

| | | |
|---|---|---|
| 2006/0128592 A1* | 6/2006 | Ross et al. .................... 510/439 |
| 2007/0135006 A1 | 6/2007 | Michaels |
| 2008/0083420 A1* | 4/2008 | Glenn et al. ................. 132/208 |
| 2009/0176675 A1* | 7/2009 | Peffly et al. .................. 510/121 |
| 2010/0175704 A1* | 7/2010 | Gueret .......................... 132/200 |
| 2011/0120487 A1* | 5/2011 | Rollat-Corvol et al. ...... 132/200 |
| 2011/0152150 A1* | 6/2011 | Bernard ........................ 510/136 |
| 2011/0180449 A1* | 7/2011 | Rubin ........................... 206/581 |
| 2011/0272304 A1* | 11/2011 | Wahal et al. .................. 206/223 |
| 2011/0308992 A1* | 12/2011 | Bahcall ......................... 206/581 |
| 2012/0076747 A1* | 3/2012 | Bierganns et al. ......... 424/70.12 |
| 2012/0097180 A1* | 4/2012 | Harris et al. ................. 132/200 |
| 2012/0171264 A1* | 7/2012 | Bernet et al. ................. 424/401 |
| 2012/0282190 A1* | 11/2012 | Hammer ......................... 424/47 |
| 2012/0325258 A1* | 12/2012 | Tan et al. ...................... 132/208 |
| 2014/0000643 A1* | 1/2014 | Swaile et al. ................. 132/202 |
| 2014/0161737 A1* | 6/2014 | Samain et al. .................. 424/43 |
| 2014/0345640 A1* | 11/2014 | Knappe et al. ............... 132/203 |

FOREIGN PATENT DOCUMENTS

| | | |
|---|---|---|
| DE | 20109450 U1 | 1/2002 |
| EP | 2777770 A1 * | 9/2014 |
| FR | 2867066 A1 | 9/2005 |
| GB | 1175278 A | 12/1969 |
| JP | 2002266147 A2 | 9/2002 |
| WO | WO2011056625 A1 | 5/2011 |

OTHER PUBLICATIONS

European Search Report in EP application EP 11 17 8055, dated Mar. 19, 2012 with Written Opinion.
PCT International Search Report in PCT application PCT/EP2012/064023 dated Sep. 24, 2013 with Written Opinion.
European Search Report in EP application EP 11 17 8056 dated Mar. 19, 2012 with Written Opinion.
IPRP1 in PCTEP2012064023 dated Feb. 25, 2014.
IPRP1 in PCTEP2012064031 dated Feb. 25, 2014.

* cited by examiner

HAIR CLEANING KIT

The present invention relates to a kit and method of using the kit for cleaning hair.

Hair and other soft surfaces are conventionally cleaned with liquid based shampoos. An alternative to liquid based shampoos are dry shampoos which do not use water to clean. However, dry shampoos, for the hair, are not particularly popular with the consumer, largely because they are inefficient in cleaning the hair and do not leave the hair with desirable sensory attributes.

Hair is usually cleaned using dry shampoo, by applying the dry shampoo to the hair followed by its removal. However, removal of the dry shampoo can leave the hair with a "fly away" appearance.

The present invention provides a method and kit for cleaning hair without the use of water and without causing the hair to have a "fly away" appearance.

SUMMARY OF THE INVENTION

The present invention provides a kit for cleansing hair comprising:
 a) a dry shampoo, in which the dry shampoo comprises a particulate material; and
 b) a separate substrate comprising a surfactant selected from the group consisting of nonionic, anionic, amphoteric and mixtures thereof.

The invention further relates to a method of cleaning hair comprising the following steps:
 a) applying to the hair a dry shampoo, said dry shampoo composition comprising particulate material followed by:
 b) wiping the hair with a substrate comprising a surfactant selected from the group consisting of nonionic, anionic, amphoteric and mixtures thereof.

In a third aspect the invention relates to the use of a substrate comprising a surfactant selected from the group consisting of nonionic, anionic, amphoteric and mixtures thereof to mitigate the flyaway appearance of hair.

In the context of the present invention an absorbing/adsorbing powder material is defined as a material capable of absorbing/adsorbing oily and fatty materials, especially those found in sebum.

DESCRIPTION OF THE INVENTION

Figure 1:
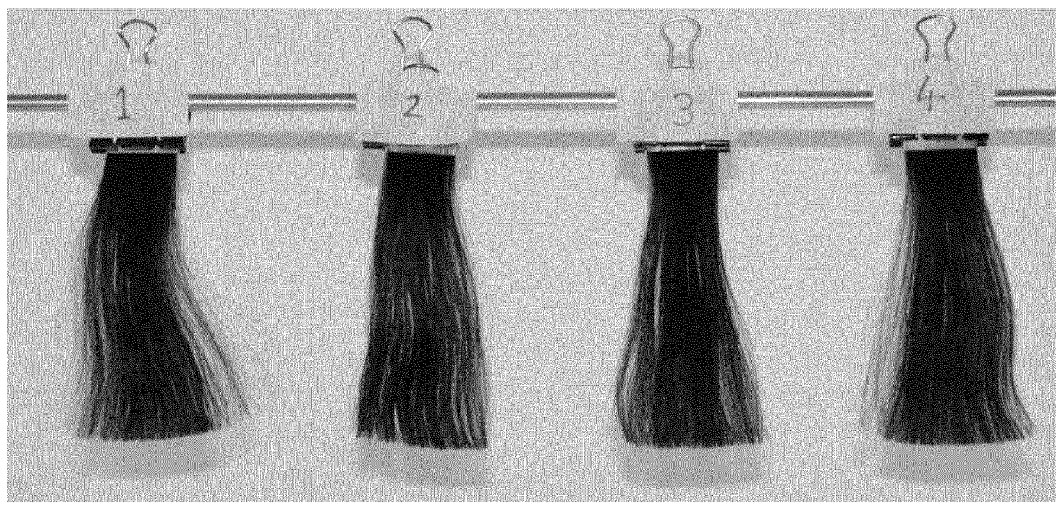
FIG. 1 is a photograph showing hair switches treated as described in the Examples.
Figure 2:
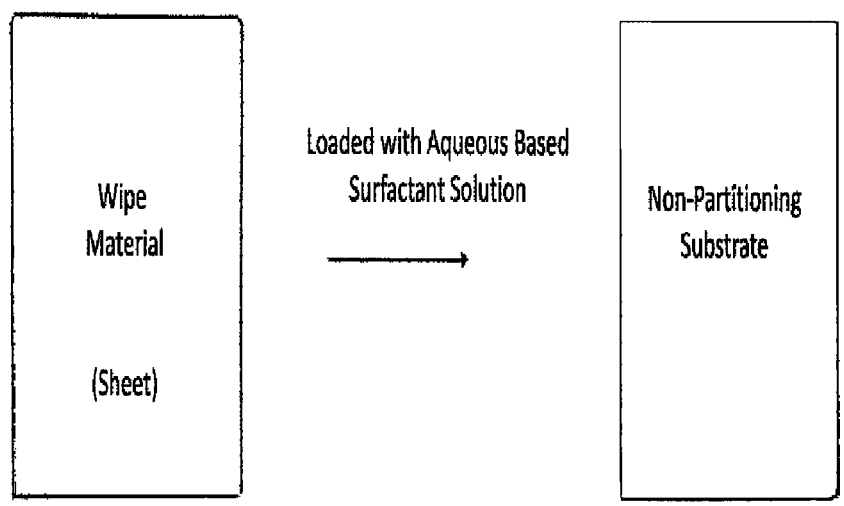
FIG. 2 is a schematic drawing of a non-partitioning substrate in which the wipe material is a sheet.

The present invention relates to kit and method for cleaning hair.

Dry shampoos are cleaning products that do not require the use of water to achieve cleaning of the surface. The dry shampoos of the present invention comprise a particulate material, the particulate material is preferably capable of adsorbing and/or absorbing oily material.

Such particulate material may be selected from the group consisting of starch, modified starch, talcum, silicone elastomer and mixtures thereof. Preferably the absorbing powder material is a starch (for example corn starch) or modified starch material. Most preferred are aluminium octenyl succinate starch and/or rice starch.

The level of absorbing powder base is at least 3 wt %, more preferably at least 5 wt % of the total composition. If the shampoo composition is a powdered composition it preferably comprises at least 50 wt % of the total composition of an adsorbing powder material.

The dry shampoo is preferably a non aqueous based cleansing composition.

Preferred formats are powdered compositions or sprays, particularly advantageous are aerosol sprays.

It is advantageous if the dry shampoo of the invention is not an aqueous based product, preferably it comprises less than 2 wt % of the total composition of water, more preferably less than 1 wt % water, most preferably less than 0.5 wt % of water.

In the case that the composition is used in aerosol form the composition is preferably applied at a distance of 20 to 40 cm from the substrate, preferably hair, and after being allowed to act for a short time may be removed.

If used as a powder, the powdered composition is shaken onto the substrate, in particular hair and after being allowed to act for a short time may be removed by combing or brushing.

The sprays of the invention can utilise any of the conventional propellants to deliver the material as a spray. Examples of suitable propellants include materials such as trichlorofluoromethane, dichlorodifluoromethane, difluoroethane, dimethylether, propane, n-butane or isobutane. Hydrocarbon based propellants are preferred.

The level of propellant can be adjusted as desired but is generally from about 20% to about 90% by weight based on total weight, preferably from 50 to 80%, by weight of the total composition.

Suitable spray containers are well known in the art and include conventional, non-aerosol pump sprays i.e., "atomisers", aerosol containers or cans having a propellant, as described above, and also pump aerosol containers utilising compressed air as the propellant.

The composition may further comprise an anticaking agent such as silica.

The composition can contain a lower (C1 to C5) chain alcohol, preferably ethanol. It is preferable the level of lower chain alcohol is present from a level of 1 wt % to 10 wt % of the total composition, more preferably from 3 to 8 wt %. These levels are particularly advantageous in an aerosol based product.

Preferably the dry shampoo comprises less then 2 wt % of the total composition of surfactant, more preferably less then 0.5 wt %, most preferably less than 0.1 wt %.

Dry shampoos in accordance with the invention can naturally also include additions conventional in hair cosmetic preparations such as perfumes, silicones and emollients.

The kit of the present invention comprise a substrate, preferably the substrate does not divide the hair, thus the substrate is not a comb or a brush. Preferably the substrate is a sheet, more preferably a flexible sheet.

Preferably the substrate is water insoluble. By "water insoluble" is meant that the substrate does not dissolve in or readily break apart upon immersion in water (at 20° C.). The water insoluble substrate is the implement or vehicle for removing the dry shampoo and sebum from the hair.

A wide variety of materials can be used as the substrate. Preferred embodiments employ nonwoven substrates since they are economical and readily available in a variety of materials. By nonwoven is meant that the layer is comprised of fibres which are not woven into a fabric but rather are formed into a sheet, mat, or pad layer.

The fibres can either be random (i.e., randomly aligned) or they can be carded (i.e. combed to be oriented in primarily one direction). Furthermore, the nonwoven substrate can be composed of a combination of layers of random and carded fibres.

Nonwoven substrates may be comprised of a variety of materials both natural and synthetic. By natural is meant that the materials are derived from plants, animals, insects or by-products of plants, animals, and insects. By synthetic is meant that the materials are obtained primarily from various man-made materials or from natural materials which have been further altered. The conventional base starting material is usually a fibrous web comprising any of the common synthetic or natural textile-length fibres, or mixtures thereof.

Cellulosic fibres are preferred. Non-limiting examples of cellulosic fibres include those selected from the group consisting of wood pulp fibres, cotton fibres, hemp fibres, jute fibres, flax fibres, and mixtures thereof. Wood pulp fibres are preferred while all cotton fibres (e.g. cotton pads) are normally avoided.

Polyester is a preferred synthetic fibres. Particularly preferred are mixtures of synthetic and natural fibres. Most preferred are mixtures of polyester and cellulosic fibres.

The substrate comprises a surfactant selected from an anionic, nonionic or amphoteric/zwitterionic surfactant. Anionic surfactants are particularly preferred.

Preferred anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

More preferred anionic surfactants are sodium oleyl sulpho succinate, ammonium lauryl sulphosuccinate, ammonium lauryl sulphate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

Preferred amphoteric and zwitterionic surfactants include, alkyl betaines, alkyl amidopropyl betaines, alkyl sulphobetaines (sultaines), alkyl glycinates, alkyl carboxyglycinates, alkyl amphopropionates, al kylamphoglycinates, alkyl amidopropyl hydroxysultaines, acyl taurates and acyl glutamates, wherein the alkyl and acyl groups have from 8 to 19 carbon atoms. More preferred amphoteric and zwitterionic surfactants are lauryl amine oxide, cocodimethyl sulphopropyl betaine and most preferably lauryl betaine, cocamidopropyl betaine and sodium cocamphopropionate.

The surfactant may be a nonionic surfactant. Preferred nonionic surfactants are condensation products of aliphatic ($C_8$-$C_{18}$) primary or secondary linear or branched chain alcohols or phenols with alkylene oxides, usually ethylene oxide and generally having from 6 to 30 ethylene oxide groups.

The total amount of surfactant on the substrate is preferably from 0.1 wt % to 5 wt % of the total weight of the wipe, more preferably form 0.2 wt % to 2 wt %.

Preferably the surfactant is applied to the wipe as a solution, more preferably the solution comprises from 0.1 wt % to 5 wt % of surfactant, more preferably from 0.2 wt % to 3 wt % of surfactant.

It is highly preferred if the solution is an aqueous based solution.

The wipe preferably comprises a 3:1 to 1:3 weight ratio of wipe material to surfactant solution, more preferably a 1:2 to 2:1 weight ratio of wipe material to surfactant solution.

The invention will now be illustrated by the following non-limiting Examples:

Comparative examples are illustrated by a letter, examples of the invention are illustrated by a number.

EXAMPLES 1) 150 mg approx, of model human sebum was massaged into each of four, 2.5 g, 6" length hair switches. Distribution was uniform across the switches and all appeared oily. The composition of the model sebum is given in table 1.

TABLE 1

Composition of model human sebum used to soil hair switches prior to cleaning.

| Name | Supplier | Level (%) in model sebum |
|---|---|---|
| Oleic acid (FATTY ACID) | VWR | 8 |
| Isostearic acid (FATTY ACID) | Croda | 4.1 |
| Tricaprin (TRIGLYCERIDE) | Sigma | 1.8 |
| Triolein (65%) (TRIGLYCERIDE) | Sigma-Aldrich | 28.2 |
| Triisostearin (TRIGLYCERIDE) | Croda | 9.2 |
| Oleyl oleate (WAX ESTER) | Cognis | 11.9 |
| Myristyl myristate (WAX ESTER) | Croda | 11.9 |
| Isostearyl isostearate (WAX ESTER) | Croda | 6 |
| Squalene | Sigma-Aldrich | 13.8 |
| Cholesterol oleate | Alfa-Aesar | 3.4 |
| Cholesterol | Sigma-Aldrich | 1.7 |

2) Cleaning:

Each switch was sprayed for 2 seconds with a dry shampoo of table 2 to deposit approximately 20 mg of product per gram of hair. A 21.6 cm×21.6 cm (8.5"×8.5") non-woven wipe of 45:55 wt ratio of polyester/cellulose comprising a surfactant in some cases, as in table 3 was rubbed along each switch ten times. A comb was passed over the hair once to align the hair. This process of spraying, wiping and combing was then repeated once more due to the high loading of model sebum applied at step 1.

TABLE 2

Dry shampoo composition

| INCI Nomenclature | % By Weight |
|---|---|
| Alcohol Denat | 7.9 |
| Isopropyl Myristate | 0.25 |
| Aluminum Starch Octenylsuccinate | 7.5 |
| Silica | 0.2 |
| Fragrance | 0.3 |
| Propane | 12.3 |
| Isobutane | To 100 |

TABLE 3

Wipe 1, Wipe 2 and Wipe 3 were loaded with 0.5% solutions applied at 1:1 weight ratio of solution to wipe.

Wipe A no surfactant solution (corresponds to switch numbered 1 in the image of FIG. 1).
Wipe 1 dodecyl(dimethyl)amine oxide, (Empigen OB), (corresponds to switch numbered 2 in the image of FIG. 1).
Wipe 2 polyoxyethylene sorbitan monolaurate, (Tween 20), (corresponds to switch numbered 3 in the image of FIG. 1).
Wipe 3 sodium lauryl (1EO) ether sulphate (Texapon N701), (corresponds to switch numbered 4 in the image of FIG. 1).

FIG. 1 shows switches treated with examples A and 1, 2 and 3, following the cleaning procedure.

It can be seen that switches treated with the examples of the invention appear less fly away than the comparative example.

The invention claimed is:
1. A kit for cleansing hair comprising:
 a) a dry shampoo, in which the dry shampoo comprises a particulate material capable of absorbing/adsorbing oily material; and
 b) a separate non-partitioning substrate comprising a wipe material loaded with an aqueous based solution wherein:
  the aqueous based solution comprises a surfactant selected from the group consisting of nonionic, anionic, and amphoteric surfactant, and mixtures thereof,
  the aqueous based solution has a surfactant concentration of from 0.1 to 5 wt. % based on the total weight of the aqueous based solution, and
  the weight ratio of the wipe material to the aqueous based solution with which the wipe material is loaded is from 3:1 to 1:3, and
wherein the dry shampoo is in the form of an aerosol composition, the aerosol composition comprising, based on the total weight thereof, at least 50 wt % of propellant.

2. A kit according to claim 1 in which the wipe material is a sheet.

3. A kit according to claim 2 in which the sheet is flexible.

4. A kit according to claim 2 in which the sheet comprises a non-woven material.

5. A kit according to claim 2 in which the sheet comprises cellulose fibre.

6. A kit according to claim 5 in which the sheet further comprises polyester fibre.

7. A kit according to claim 1 in which the particulate material is a modified starch.

8. A kit according to claim 7 in which the particulate material is an aluminium octenyl succinate starch.

9. A method of cleaning hair comprising the following steps:
 a) applying to the hair a dry shampoo, said dry shampoo comprising a particulate material capable of absorbing/adsorbing oily material, wherein the dry shampoo is in the form of an aerosol composition, the aerosol composition comprising, based on the total weight thereof, at least 50 wt % of propellant; followed by
 b) wiping the hair to which the dry shampoo has been applied with a non-partitioning substrate comprising a wipe material loaded with an aqueous based solution that comprises a surfactant selected from the group consisting of nonionic, anionic, and amphoteric surfactant, and mixtures thereof,
wherein:
said aqueous based solution has a surfactant concentration of from 0.1 to 5 wt. %, based on the total weight of the aqueous based solution, and
the weight ratio of the wipe material to the aqueous based solution with which the wipe material is loaded is from 3:1 to 1:3, and wherein wiping the hair with the non-partitioning substrate mitigates fly-away appearance of the hair to which the dry shampoo has been applied.

10. A method according to claim 9 wherein the surfactant is anionic surfactant.

11. A kit according to claim 1 wherein the surfactant is an ionic surfactant.

* * * * *